United States Patent [19]

Friedrichs

[11] Patent Number: 4,887,787
[45] Date of Patent: Dec. 19, 1989

[54] MEANS FOR MOUNTING HARDWARE OR FITTINGS, ESPECIALLY SHELVES AND HOLDERS

[75] Inventor: Bernd Friedrichs, Arolsen, Fed. Rep. of Germany

[73] Assignee: Hewi Heinrich Wilke GmbH, Fed. Rep. of Germany

[21] Appl. No.: 263,175

[22] Filed: Oct. 27, 1988

[30] Foreign Application Priority Data

Oct. 30, 1987 [DE] Fed. Rep. of Germany ....... 8714446

[51] Int. Cl.[4] .............................................. F16M 13/00
[52] U.S. Cl. ..................................................... 248/551
[58] Field of Search .................. 248/551, 224.4, 223.4, 248/224.2, 224.1, 309.1, 359 R, 359 F, 360

[56] References Cited

U.S. PATENT DOCUMENTS

| 2,343,750 | 4/1944 | Conran | 248/551 X |
| 3,389,883 | 6/1968 | Johnson | 248/359 R |
| 4,270,821 | 6/1981 | Verdesca | 248/224.4 X |
| 4,709,897 | 12/1987 | Mooney | 248/551 |

FOREIGN PATENT DOCUMENTS

| 1829299 | 4/1961 | Fed. Rep. of Germany . |
| 2535894 | 3/1979 | Fed. Rep. of Germany . |
| 2056723 | 4/1979 | Fed. Rep. of Germany . |
| 2437051 | 11/1981 | Fed. Rep. of Germany . |
| 3105185 | 9/1982 | Fed. Rep. of Germany . |
| 3105216 | 9/1982 | Fed. Rep. of Germany . |
| 3239106 | 2/1984 | Fed. Rep. of Germany . |
| 3105217 | 4/1987 | Fed. Rep. of Germany . |
| 3102191 | 5/1987 | Fed. Rep. of Germany . |
| 628232 | 2/1982 | Switzerland . |
| 1223738 | 3/1971 | United Kingdom . |

Primary Examiner—Ramon O. Ramirez

[57] ABSTRACT

The invention relates to a mounting device on hardware or fittings, especially shelves and holders, which contain at least one base part which is to be fastened to a wall or the like and which has a bearing surface which can be pressed onto the base part and completely conceals it in the installed state. To create a theft-proof connection between these parts two kinds of fastening means are used. The one fastening means associated with the fully installed state of the cover part prevents, in the assembled state, any even partial unintentional separation of the cover part from the base part, and in the separated state permits the cover part to be removed completely. The other fastening means does permit a partial removal of the cover part from the base part in the assembled state, and complete removal in the separated state, but is accessible only when the cover part is in an at least partially removed state of the cover part which can be achieved only after the release of the first fastening means.

16 Claims, 6 Drawing Sheets

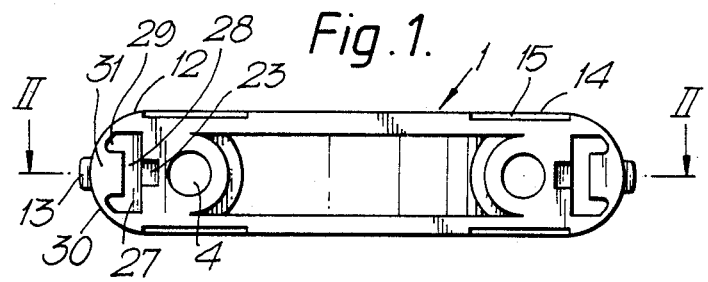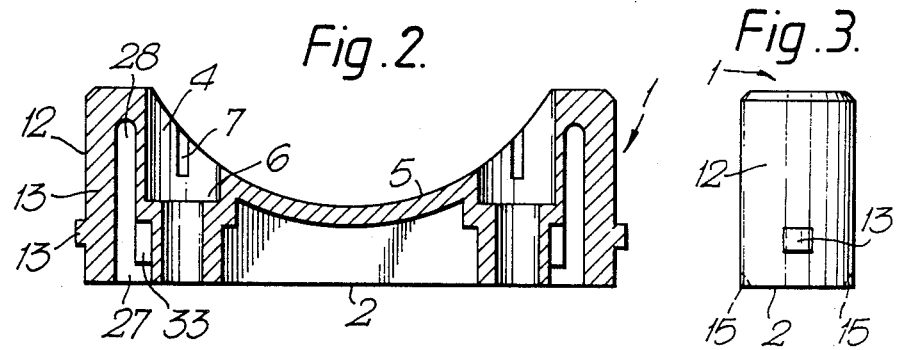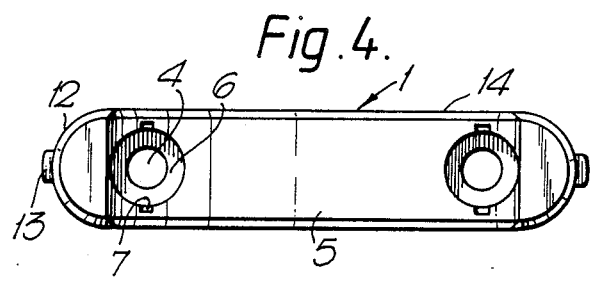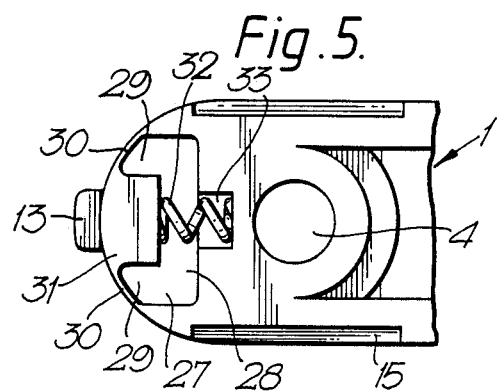

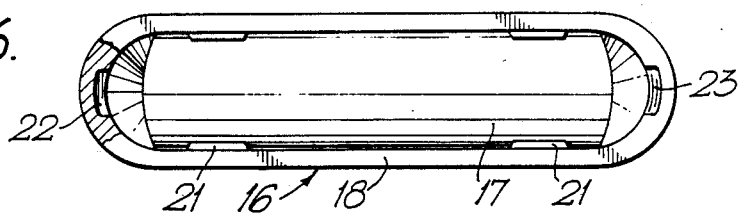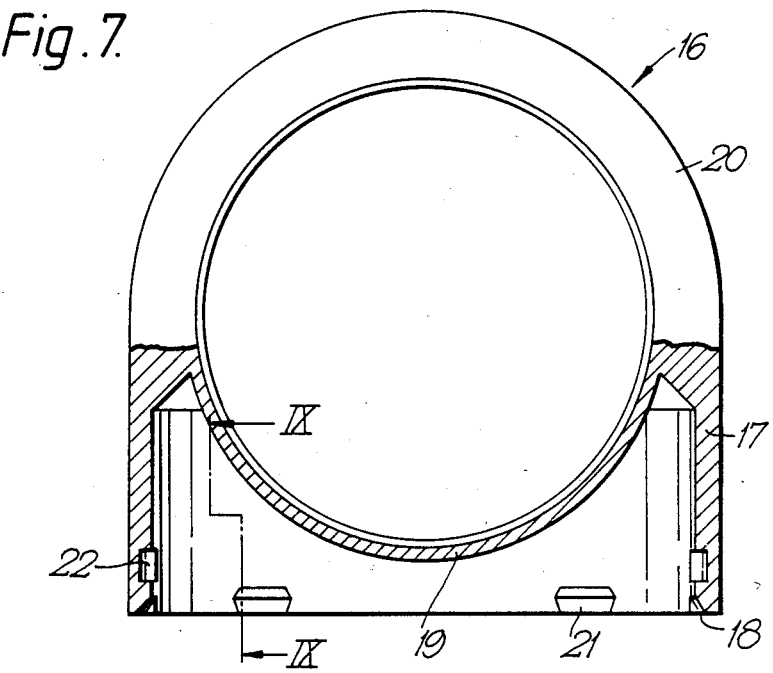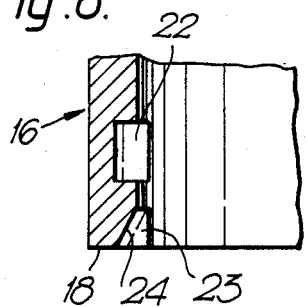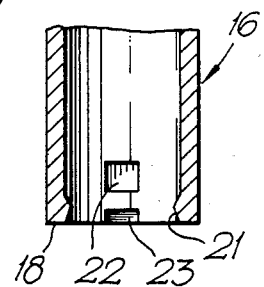

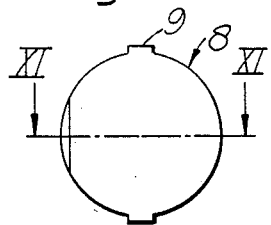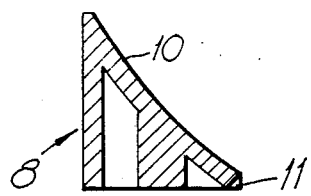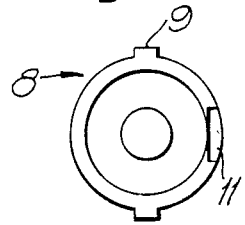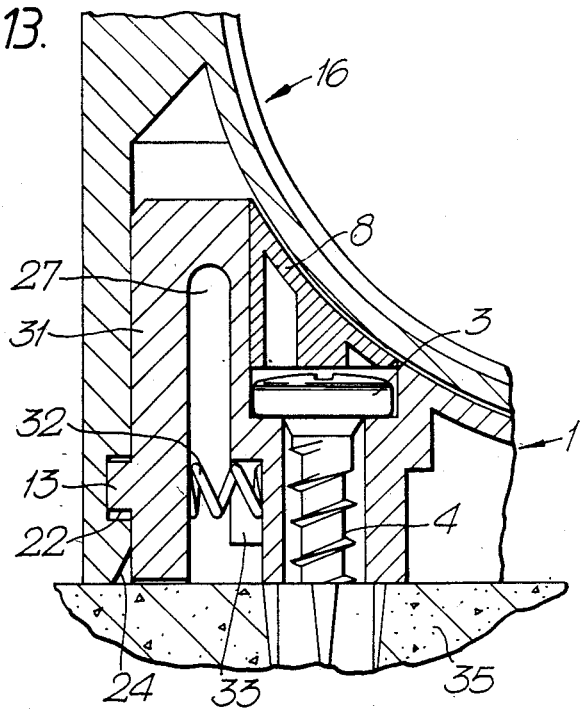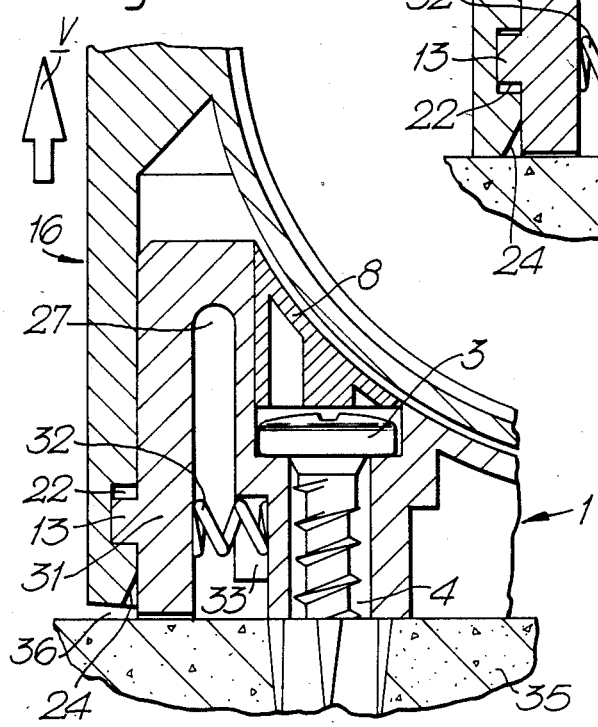

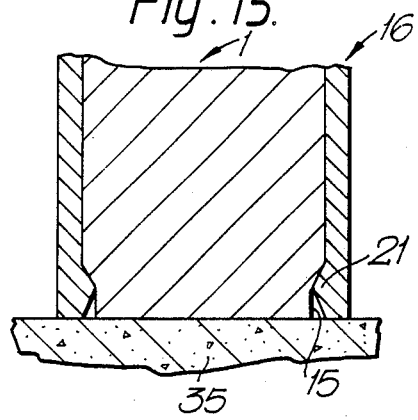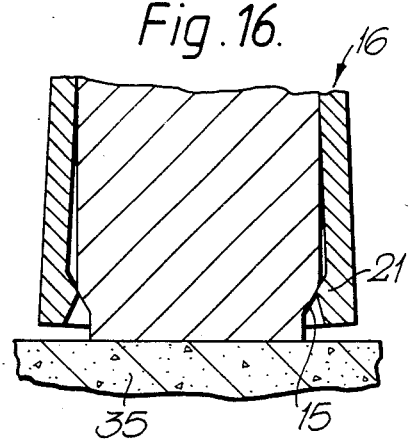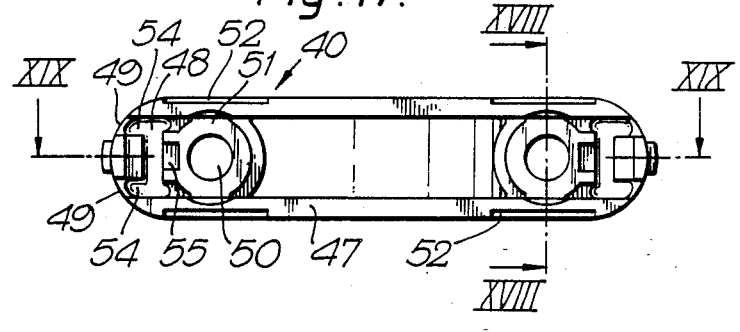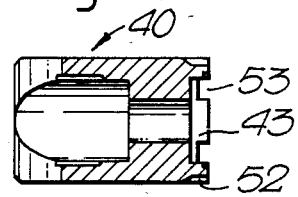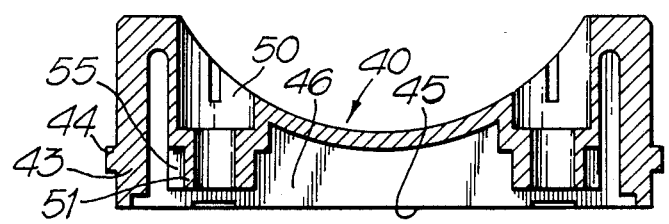

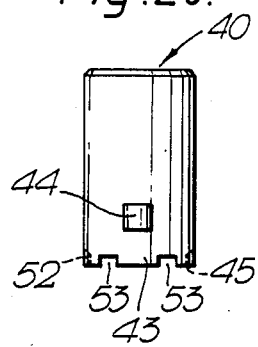
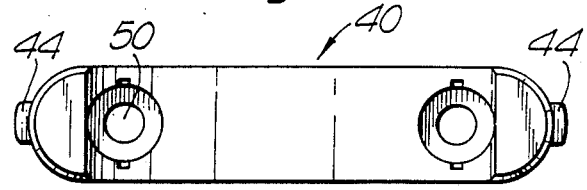
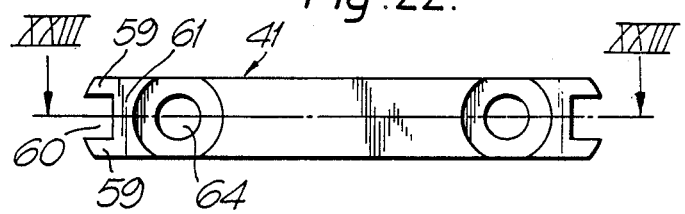
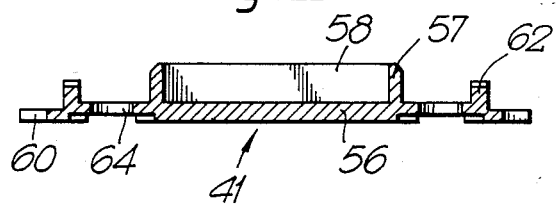
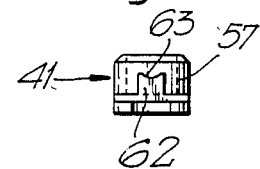
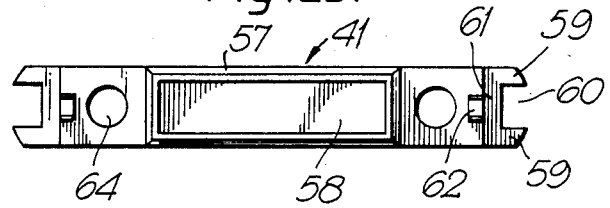

MEANS FOR MOUNTING HARDWARE OR FITTINGS, ESPECIALLY SHELVES AND HOLDERS

BACKGROUND OF THE INVENTION

The invention relates to a mounting means on hardware or fittings, especially brackets or holders which have at least one base part with a bearing surface for fastening to a wall or the like and a cover part which can be pressed onto the base part and covers it completely in the installed state, having first fastening means associated with the fully installed state of the cover part, which in its assembled state prevents even partial unintentional removal but in the separated state permits complete removal of the cover part from the base part.

Known mounting devices of this kind are used, for example, on soap dishes, drinking glass holders, ashtrays, multipurpose shelves or the like, but also on push plates on doors, door plates, rosettes, letter slot covers, or the like, especially in the household and sanitary areas. They have, for example, matching undercuts (DE-OS Nos. 20 56 723 and 24 37 051) which when the cover part is in the installed state form a snap fastening between the cover part and the base part. Such mounting means are widely used and therefore, when they are employed in areas exposed to the public, e.g., in schools, swimming pools or the like, they are not very theft-resistant. The same considerations apply to mounting devices with pin fastenings.

Mounting devices of the kind described above have therefore been disclosed whose fastening means have spring-loaded pins mounted in the bottom parts (DE-OS Nos. 31 02 191, 31 05 216 and 31 05 217) or resilient tongues provided on the cover or base parts (DE-OS No. 25 35 894). These spring-loaded pins or tongues are engaged in the installed state in a recess or behind a projection or the like on the other part and can be forced out of the engaged position through an opening in the cover part with a finger or tool when the cover part is to be removed from the base part.

Often a theft-proofing means is additionally provided such that the spring pins or resilient tongues can be disengaged only in a very specific position and/or preferably only through a very small opening. To remove the cover part, therefore, either an exact knowledge of the theft-proofing device and/or a special tool are necessary.

Even mounting devices of the kind last described are not always sufficiently theft-proof, because the openings necessary for releasing the catch are indeed in a concealed location but cannot be made entirely invisible. Aside from that, these openings permit the entry of dirt, soap, moisture or the like, which must be avoided, especially when the fastening means is used in wet rooms, in order to prevent corrosion, mildew or the like in the cavities between the bottom parts and top parts, and to reduce to a minimum the need for cleaning and maintaining the upper and base parts. The same applies to mounting means having pins which can be released only after a locking means has been unlocked through an opening formed in the cover part (DE-OS No. 25 35 894).

It is the purpose of the invention to construct the mounting means referred to above such that, in spite of the presence of a special theft-proof lock, no openings need to be provided in the cover part.

SUMMARY OF THE INVENTION

This purpose is accomplished in accordance with the invention by providing second fastening means which in their assembled state permit a partial withdrawal but in their separated state permit a complete withdrawal of the cover part from the base part, and which are accessible only when the cover part is in the at least partially withdrawn state, which can be brought about after releasing the first fastening means.

The invention offers the advantage that the second fastening means opens up entirely new approaches to theft-proofing. Even if one might succeed in releasing the fastening provided by the first fastening means, the complete stripping of the cover part from the base part is not yet possible. For this purpose it would also be necessary to release the fastening provided by the second fastening means, preferably with a second tool, so that unauthorized removal of the cover part and then of the base part is at least made very difficult. Furthermore, no opening in the cover part is necessary to permit the cover part to be removed from the base part, so that the cover part can be provided with a completely closed, smooth and easily cleaned surface, and the entry of dirt, moisture or the like into the space inside of the cover part is prevented.

Additional advantageous features of the invention will be found in the subordinate claims.

BRIEF DESCRIPTION OF THE DRAWINGS

The invention will be further explained below by means of embodiments in conjunction with the appended drawing, wherein:

FIG. 1 is a bottom view of a base part of a wall fitting with a mounting means in accordance with the invention;

FIG. 2 is a section taken along line II—II of FIG. 1;

FIG. 3 is an end view of the base part of FIG. 1;

FIG. 4 is a top view of the base part of FIG. 1;

FIG. 5 is an enlarged detail of the base part of FIG. 1 with a spring inserted;

FIG. 6 is a partially cut-away bottom view of a cover part intended for the base part of FIGS. 1 to 5;

FIG. 7 is a partially cut-away top view of the cover part of FIG. 6;

FIG. 8 is an enlarged detail Z of FIG. 7;

FIG. 9 is a section along line IX—IX of FIG. 7;

FIGS. 10 to 12 are enlarged representations of the top view, the section along line XI—XI of FIG. 10, and the bottom view of a plug for the base part of FIGS. 1 to 5, respectively;

FIGS. 13 and 14 are enlarged sections corresponding to FIGS. 2, 7 and 11 through the entire wall fitting in the installed state in two different positions;

FIGS. 15 and 16 are fragmentary front views of the fitting in two different positions corresponding to FIGS. 13 and 14;

FIG. 17 is a bottom view of a second embodiment of the base part;

FIGS. 18 and 19 are sections along lines XVIII—XVIII and XIX—XIX of FIG. 17;

FIGS. 20 and 21 are an end view and a top view, respectively, of the base part of FIG. 17;

FIGS. 22 to 25 show the bottom view, the section along line XXIII—XXIII of FIG. 22, a side view, and the top view of a masking plate for the base plate of FIGS. 17 to 21;

DESCRIPTION OF PREFERRED EMBODIMENTS

Figure 26:
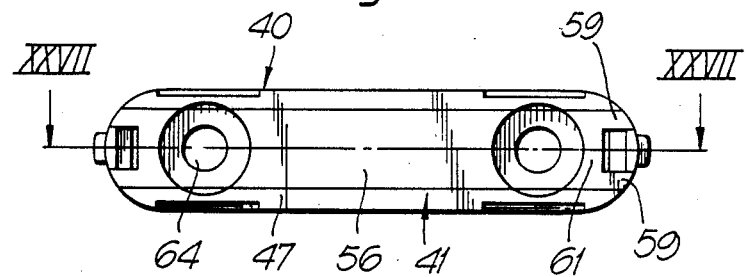
FIGS. 26 and 27 are a bottom view and a section along line XXVII—XXVII of FIG. 26 of the base part and the masking plate in accordance with FIGS. 17 to 25 in the assembled state.

In FIGS. 1 to 5, a base part 1 of a wall fixture in the form of a mouth-rinsing cup holder contains a substantially planar bearing surface 2 to lie flat against a wall or the like, to which it is fastened by screws 3 (FIGS. 13, 14) which pass through screw holes 4. The screw holes 4 run from the bearing surface 2 to the opposite surface 5, which is concavely curved in this special case, of the base part 1, and have each a narrowed cross section beginning at the middle of their length to create shoulders 6 to accommodate the heads of the mounting screws 3. Moreover, the wall sections adjoining the screw holes 4 have grooves 7 at their ends adjoining the surface 5.

Plugs 8 (FIGS. 10 to 12) can be pressed into the screw holes. These plugs 8 have a cross section corresponding to the cross section of the screw holes 4 and are provided with radial projections 9 intended for anti-rotational introduction into the grooves 7. At their one end the plugs 8 are each provided with a concavely curved surface 10 corresponding to the surface 5 of the base part 1. At the same time the length of the grooves 7 and projections 9 is such that the surfaces 10 of the plugs form step-less continuations of the surface 5 of the base part 1 separated only by a fine seam when the projections 9 abut against the bottom ends, in FIG. 2, of the grooves 7, and that at the same time there will still be sufficient room between the plugs 8 and the shoulders 6 for the heads of the screws (FIGS. 13, 14). After the installation of the plugs 8, therefore, the base part 1 will have a smooth surface 5 completed by the surfaces 10. In the bottom margin of the plug 8 a small indentation 11 can be formed with a wall section running at an angle to the surface 10, which permits the plug 8 to be removed after its introduction into one of the screw holes 4.

The base part 1 has a substantially flattened-oval external cross section and is provided at its short, curved ends with fastening means in the form of radial projections 13 which terminate slightly above the bearing surface 2. On each of its long, straight side surfaces 14 the base part 1 has at least one fastening means in the form of an undercut 15 (FIGS. 1 and 3) or of an outward projection or the like; this undercut 15, indicated in broken lines in FIG. 3, can best be at the edge of the bearing surface 2 or terminate close to same.

In FIGS. 6 to 9, a cover part 16 matched to the base part 1 has a cap-like holding section 17 with a flattened oval internal cross section corresponding to the external cross section of the base part 1. The holding section 17 can be pressed onto the base part 1 and then covers the latter completely. The holding section 17 has at its free end a flattened oval abutment surface 18, and at its opposite end a concavely curved wall section 19 adapted to the surface 5 of the base part. The holding section 17 is adjoined by a semicircular rim section 20 which together with wall section 19 forms a cylindrical ring and thus forms a holder in which, for example, a mouth rinsing cup, an ash tray or the like can be inserted.

The cover part 16 is provided on its straight wall section adjoining the bearing surface 18 with internal fastening means in the form of undercuts 21 or inwardly reaching projections or the like, which are to cooperate with the undercuts 15 on the base part 1. Furthermore, the holding section 17 has on the insides of its curved, short wall sections the fastening means in the form of a recess 22 which is associated with one of the projections 13 of the base part 1 and can completely contain the latter. In the direction perpendicular to the bearing surface 18 the recess 22 is slightly longer than the length of the projection 13 measured perpendicular to the bearing surface 2. In the area of the short wall sections there is furthermore formed, under each recess 22, a recess 23 adjoining the bearing surface 18 and defined by a wall which is in the form of an entry ramp 24 and therefore slopes toward the outside.

To permit both the installation and removal of the cover part 16 in spite of the projections 13 of the base part 1, the base part 1 has in each section situated in back of the projections 13, as shown especially in FIG. 5, a cavity 27 in the nature of a blind hole open at the bearing surface 2, whose axis is parallel to the axis of the screw holes 4. The cavities 27 have a U-shaped cross section and thus they have two branches 29 joined by a transverse section 28, which are substantially parallel to the long, straight lateral surfaces 14 of the base part. These branches 29 run to a point close to the end surface 12, so that very thin, flexible wall sections 30 are formed, which leave standing between them a tongue 31 or section of wall that is resiliently held on the base part 1, bears one of the projections 13, and can be pressed radially inwardly. To assure that this movement will not fail to be sufficiently reversible resiliently on account of material fatigue or the like, or that the return force of the thin membrane or wall sections 30 will be adequate, on the inside of each tongue 31 the one end of a spring 32 in the form of a compression spring thrusts whose other end thrusts against the bottom of a section 33 of the cavity 27. This section 33 is disposed on the back of the transverse section 28 and runs from the bearing surface 2 to a point in back of the projection 13 (FIG. 2), so that the spring 32 can be inserted from the bearing surface side and pressed to the end of section 33, and thus can be correctly positioned.

According to FIGS. 13 to 16, the installation and removal of the parts described in conjunction with FIGS. 1 to 12 is performed as follows:

After the base part 1 is fastened to a wall 35 or the like by means of the screws 3, first the plugs 8 are inserted into the open ends of the screw holes 4. Then the cap-like holding section 17 of the cover part 16 is pressed onto the base part 1, while the undercuts 21 slide on its lateral surface 14. Preferably, the undercuts and/or holding section 17 are made of a flexible material, such as plastic, so that they can be deflected laterally when pressed on the base part 1 as shown in FIG. 16.

As the pressing on of the holding section 17 continues, its lead-in ramps 24 slip over the associated projections 13 of the base part 1. This has the result that its tongues 31 are forced inwardly against the force of springs 32, toward the transverse portion 28 of the cavity 27, the flexible wall sections 30 (FIGS. 1 and 5) acting as joints or hinges. As soon as the recesses 22 are at the level of the projections 13, the latter with the tongues 31 snap radially outward under the influence of the elastic restoring forces of the wall sections 30 or springs 32, until they reach into the recesses 22 and thus produce a junction between the base part 1 and the cover part 16.

As the pressing of the cover part 16 continues, which is possible on account of the greater length of the recesses 22 in comparison to the projections 13, the undercuts 21 of the cover part 16 snap behind the complementary undercuts 15 of the base part 1. The cover part 16 is thus tightly fastened to the base part 1, in accordance with FIGS. 13 and 15, since the base part and the holding section 17 have equal cross-sectional shapes. Axial free play of the cover part 16 perpendicular to the wall 35 or the like is prevented by the fact that the undercuts 15 and 21 are so disposed and shaped that the abutment surface 18 (FIG. 7) of the cover part 16 lies tightly all around against the wall 35 or the like after the snap fastening is made and only a hairline seam remains between the two.

The undercuts 15, 21, form first fastening means which in the assembled state prevent unintentional removal of the cover part 16 from the base part 1. Neither is any partial removal of the cover part 16 possible due to the lack of axial free play. If, however, the undercuts 21 are forced away over the undercuts 15 with the aid of a tool, the cover part 15 can easily be removed entirely from the base part 1 if the projections 13 and recesses 22 are lacking.

The projections 13 and recesses 22 form second fastening means which also tightly fasten the cover part 16 to the base part 1, but if the first fastening means are lacking, or if they are released, the said projections and recesses permit a limited relative movement of the cover part 16 on the base part 1. The second fastening means therefore constitute an additional safeguard against unauthorized removal of the cover part 16. If the snap fastening formed by the undercuts 15 and 21 is released with a knowledge of their function, then the cover part 15 can nevertheless be shifted perpendicular to the wall only as much as corresponds to the axial free play provided for the projections 13 in the recesses 22.

If the secret is known, an authorized removal of the cover part 16 can be accomplished by releasing the fastening provided by the first fastening means (15 and 21) and then shifting the cover part 16 on the base part 1 as far as the recesses 22 allow, in the direction of an arrow v (FIGS. 14 and 16). Then, through a gap 36 (FIG. 14) thus created between the bearing surface 18 of the cover part 16 and the wall 35, pressure is exerted on each side with a tool, e.g., a screwdriver blade, against the bottom ends of the tongues 31 to flex them radially inwardly into the cavities 27. This removes the projections 13 from the recesses 22 so that now the two fastening means (13, 22) are also separated from one another and the cover part 16 can be fully removed from the base part 1. If the wall section of the cover part 16 is sufficiently flexible, it is also possible under certain circumstances to remove the two projections 13 successively out of the corresponding recesses 22 by slightly canting the cover part 16 between these two steps.

In the case of a planar wall 35 or the like, the bearing surface 18 of the cover part 16 lies tightly against it all around. Moreover, the outer surface of the cover part 16 has no openings, bores or the like. Consequently no contaminants such as dust, moisture or the like can enter into the space contained in the cover part, so that a hygienically unexceptionable arrangement is the result. Even if the bearing surface 18 of the cover part or the bearing surface 2 of the base part 1 should not lie completely flat against the wall 35 or the like, as would be possible in the area of the seams between wall tiles, the danger of interior contamination is comparatively slight, since the screw holes 4 are closed by the plugs, and moisture, dirt or the like could penetrate into the screw holes 4 and cavities 27 only from underneath.

In order largely to prevent this too, a base part 40 modified as in FIGS. 17 to 21 is preferably combined with a dust cover 41 as shown in FIGS. 22 to 25. The base part 40 is of essentially the same construction as in FIGS. 1 to 5, and accordingly has movable tongues 43 bearing projections 44 like the tongues 31, but they terminate several tenths of a millimeter, i.e., slightly above a bearing surface 45, so as to be easily movable even when the base part 40 is in the assembled state. In contrast to FIGS. 1 to 5, the base part 40 is of a cap-like configuration, which is better for its manufacture by injection molding, and accordingly it is provided with a cavity 46 which is surrounded by a lateral wall 47 adjoining the bearing surface 45, which is joined to the tongues 43 by thin wall sections 49 in the area of the cavities 27. Moreover, screw holes 50 corresponding to screw holes 4 are provided, which are surrounded by cylindrical wall sections 51 terminating above the bearing surface 45 which serve to accommodate the plugs 8. The wall sections 51 at the same time constitute lateral boundaries of the cavity 46. Furthermore, undercuts 52 corresponding to undercuts 15 are provided (FIGS. 17, 18) which are indicated in broken lines in FIG. 20. Unlike the construction seen in FIGS. 1 to 5, narrow indentations 53 adjoining the bearing surface 45 are formed on both sides of the tongues 43 (FIGS. 18 and 20). Each of the cavities 48, like the cavities 27, has two longitudinal branches 54, a transverse section connecting them, and a section 55 in the back of the latter.

The dust cover 41 has a flat base 56 whose thickness corresponds to the distance between the bearing surface 45 and the wall sections 51 of the base part 40. On its upper side the dust cover 41 is provided with a peripheral wall 57 around a cavity 58 and has an external cross section corresponding to the internal cross section of the cavity 46 in the base part 40.

At both its ends the dust cover 41 is forked and provided with two tines 59 between which there is a gap 60. The tines 59 and the web 61 between them have a cross sectional shape corresponding substantially to the cross-sectional shape of the cavities 48. In the back of the web 61 there is a projection 62 which has a cross-sectional shape corresponding to section 55 of the cavities 48 and has a concave top 63. Lastly, the dust cover 41 is provided with screw holes 64. The width of the dust cover 41 corresponds to the width of the cavity 46 in the base part 40, while its length is substantially equal to the length of the base part 40.

Figure 27:
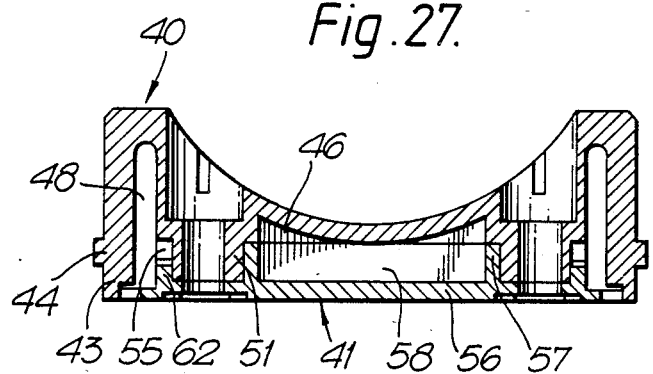

The dust cover 41 is placed against the bottom of the base part 40, as shown in FIGS. 26 and 27, such that its wall section 57 comes to rest in the cavity 46 and at the same time lies laterally against its wall sections 47. The dust cover 41 is thus centered on the base part 40. In this position the bottom of the dust cover 41 also is flush with the bearing surface 45 of the base part 40, and the straight sections of the side walls 47 lie closely against the correspondingly straight side margins of the dust cover 41. Furthermore, the webs 61 and the tines 59 completely cover the cavities 48 of the base part 40, while the tines 59 extend all the way into the indentations 53 (FIG. 20) of the base part 40, with the bottom end of the tongue 43 between them. Lastly, each projection 62 extends from underneath into section 55 of the corresponding cavity 48 such that its concave top 63 (FIG. 24) forms a boundary of the space in section 55 that is occupied by the spring 32 which is not shown (FIGS. 13, 14) and the spring 32 is blocked against movement therein. Aside from that, the system is best so arranged that the dust cover 41 can be pressed into the base part 40 with an easy fit, and so that the base part 40, after assembly, will be perfectly sealed except for narrow seams and the screw holes 50 aligned coaxially with the screw holes 64. In this case, after a cover part 16 corresponding substantially to FIGS. 6 to 9 has been pressed in place, no dirt or the like can enter the space which it envelops if the bearing surface 45 of the base part 40 does not lie perfectly flat on a wall or the like.

Otherwise, the function of the mounting means consisting of the first and second fastening means is the same as described in conjunction with FIGS. 13 to 16.

The invention is not limited to the embodiments described, which can be modified in many ways. For one thing, the base part and the cover part can be configured differently and can be adapted to any other hardware or fitting instead of a holder for a mouth rinse cup. At the same time, it is also possible by a modification for the purpose to combine a cover part with more than one base part. Instead of the plugs 8 which make it possible to produce a base part with a largely smooth surface, other plugs may be provided. It would furthermore be possible to make the cavities 27 and 48 not as blind holes but as through-bores and/or to close their top ends, and their bottom ends too if necessary, with additional plugs as long as this does not interfere with the operation of the tongues 31 and 43. Instead of the fastening means represented as undercuts 15 and 21, other elements, such as pins, can be provided, which are introduced into coaxial bores in the cover and base parts. Also, in this case it would be necessary, after pressing in the pins, first to release the second fastening means before the cover part can finally be withdrawn from the bottom part. In like manner the second fastening means could be pins reaching, for example, into elongated holes and thus to permit limited movements of the cover part perpendicular to the wall or the like.

It is furthermore apparent from the above-described embodiments that the second fastening means (13, 22 and 44) are invisible from the exterior even after the first fastening means are released. Also, the thin wall sections 30 and 49 cannot be noticed from the exterior. Therefore, unauthorized persons, if they do not know the secret, are given no hint as to how the cover part can be completely removed, even after the cover part has been partially removed from the base part. Alternatively, it is also conceivable to separate the tongues 31 and 43 from the adjacent wall sections, not by thin wall sections 30 and 49, but by narrow slits provided laterally. In this case the slits would be visible from the exterior. But when the second fastening means are configured such that the cover part can be moved only a few millimeters after the release of the first fastening means, there is no danger even in such an embodiment as this that the secret of how to open the mounting means might be accidentally revealed. Instead of the tongues 31 and 43, other elements, of course, can be provided for separating the fastening provided by the second fastening means.

The cover part and base parts as well as the dust covers can be made preferably from plastic by injection molding. The same applies to the plugs 8.

I claim:

1. Mounting means on hardware or fittings comprising at least one base part with a bearing surface for fastening to a wall or the like, and a cover part which can be pressed onto the base part and covers the same completely in the installed state, first fastening means associated with the fully installed state of the cover part and preventing in an assembled state even partial unintentional removal, but in a separated state permitting complete removal, of the cover part from the base part; and second fastening means which in assembled state permit partial withdrawal but in separated state permit a complete withdrawal of the cover part from the base part and which are accessible only when the cover part is in at least partially withdrawn state after release of the first fastening means.

2. Mounting means in accordance with claim 1, wherein the second fastening means are invisible from outside even with the cover part partially removed.

3. Mounting means in accordance with claim 1, wherein the second fastening means has an element accessible after partial removal of the cover part from the base part.

4. Mounting means in accordance with claim 3, wherein the element is a tongue which is resiliently provided on the base part and can be pressed inwardly from outside.

5. Mounting means in accordance with claim 4, wherein the tongue consists of a movable section of a wall of the base part which adjoins the bearing surface and is joined to the wall by thin, flexible wall sections.

6. Mounting means in accordance with any one of claims 1 to 5, wherein the first fastening means consists of undercuts formed in the base part and cover part and intended to produce a snap fastening.

7. Mounting means in accordance with claim 1, wherein the second fastening means is formed by at least one recess formed on an inner wall of the cover part and by a projection provided on the base part and extending with clearance into the at least one recess.

8. Mounting means in accordance with claim 4, wherein the second fastening means is formed by at least one recess formed on an inner wall of the cover part and by a projection provided on the base part and extending with clearance into the at least one recess.

9. Mounting means in accordance with claim 8, wherein the projection is formed on the tongue.

10. Mounting means in accordance with claim 9, wherein the base part has at least one cavity adjoining the bearing surface, which is defined on one side by the tongue.

11. Mounting means in accordance with claim 10, comprising a spring in the cavity and thrusting between the tongue and a confronting wall section defining the cavity.

12. Mounting means in accordance with claim 7, wherein the recess is so much larger than the projection such that the recess permits the cover part to move back and forth on the base part between a fully seated and a partially withdrawn position.

13. Mounting means in accordance with claim 1, wherein the base part is of a cap-like configuration and has a cavity open at the bearing surface, and that a dust cover completely covering the cavity and in flush alignment with the bearing surface is associated with the base part.

14. Mounting means in accordance with claim 10, wherein the base part is of a cap-like configuration and has a cavity open at the bearing surface, and that a dust cover completely covering the cavity and in flush alignment with the bearing surface is associated with the base part.

15. Mounting means in accordance with claim 14, wherein the dust cover also covers the cavity in the base part.

16. Mounting means in accordance with claim 15, wherein the dust cover is provided at its ends with fork tines, webs and projections adapted to the cross-sectional shape of the cavity.

* * * * *